US00PP36882P2

(12) United States Plant Patent
Brand

(10) Patent No.: US PP36,882 P2
(45) Date of Patent: Aug. 12, 2025

(54) ***ARONIA* PLANT NAMED 'UCONNAA001'**

(50) Latin Name: *Aronia arbutifolia*
Varietal Denomination: UCONNAA001

(71) Applicant: University of Connecticut, Farmington, CT (US)

(72) Inventor: Mark Henry Brand, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 18/964,906

(22) Filed: Dec. 2, 2024

(51) Int. Cl.
*A01H 6/74* (2018.01)
*A01H 5/08* (2018.01)

(52) U.S. Cl.
USPC ..... Plt./156

(58) Field of Classification Search
USPC ..... Plt./156, 226
CPC ..... A01H 6/74; A01H 5/02; A01H 5/08
See application file for complete search history.

*Primary Examiner* — Keith O. Robinson
(74) *Attorney, Agent, or Firm* — Cassandra Bright

(57) ABSTRACT

A new and distinct cultivar of *Aronia* plant named 'UCONNAA001' is disclosed, characterized by a significantly more compact habit than the primary commercial cultivar of red chokeberry. Plants flower early and profusely. Fruit production is abundant and early. Fruits emerge yellow then ripen to a glossy red. Fall foliage is bright red and begins early. The new cultivar is an *Aronia*, intended for garden purposes.

6 Drawing Sheets

Latin name of the genus and species: *Aronia arbutifolia*.
Variety denomination: 'UCONNAA001'.

BACKGROUND OF THE INVENTION

The new *Aronia* cultivar is a product of a planned breeding program conducted by the inventor, Mark Henry Brand in Storrs, Connecticut. The objective of the breeding program was to develop new *Aronia* varieties with shorter stature, heavy flowering, heavy fruiting, and red fall foliage color. The self-pollination resulting in this new variety was made during April of 2014 at a research nursery in Storrs, Connecticut.

The seed parent is an unpatented, proprietary selection of *Aronia arbutifolia* named 'CTred'. There is no separate pollen parent, as the new variety is the result of self-pollination. The new variety was discovered in May of 2018 by the inventor in a group of seedlings resulting from the 2014 self-pollination, in a research nursery in Storrs, Connecticut.

Asexual reproduction of the new cultivar 'UCONNAA001' was first performed during June of 2018, using softwood stem cuttings at a nursery in Storrs, Connecticut. Subsequent propagation by softwood cuttings has shown that the unique features of this cultivar are stable and reproduced true to type in 7 successive generations.

SUMMARY OF THE INVENTION

The cultivar 'UCONNAA001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UCONNAA001'. These characteristics in combination distinguish 'UCONNAA001' as a new and distinct *Aronia* cultivar:

1. Significantly more compact habit than the primary commercial cultivar of red chokeberry.
2. Early, profuse flowering.
3. Copious amounts of early-ripening fruit which emerge yellow then ripen to a glossy red.
4. Early, bright red fall foliage.

PARENT COMPARISON

Plants of the new cultivar 'UCONNAA001' are similar to plants of the parent, *Aronia arbutifolia* 'CTred' in most horticultural characteristics, however, plants of the new cultivar 'UCONNAA001' differ in the following;

1. Plants of the new variety flower more profusely than plants of the seed parent.
2. Plants of the new variety produce more fruit than plants of the seed parent.
3. Plants of the new variety are more compact than plants of the seed parent.

COMMERCIAL COMPARISON

Plants of the new cultivar 'UCONNAA001' can be compared to the unpatented commercial variety *Aronia arbutifolia* 'Brilliantissima'. These varieties are similar in most horticultural characteristics; however, 'UCONNAA001' differs in the following:

1. Plants of the new variety are more compact than plants of this comparator.
2. Plants of the new variety produce substantially more flowers and fruit than plants of this comparator.
3. Fall foliage color of the new variety develops 2 weeks earlier than fall foliage color of this comparator.

4. Flowers of the new variety open 10 to 14 days earlier than flowers of this comparator.
5. Fruits of the new variety ripen 10 to 14 days earlier than fruits of this comparator.

BRIEF DESCRIPTION OF THE PHOTOGRAPHS

The accompanying photograph in FIG. 1 illustrates in full color a typical field grown plant of 'UCONNAA001' in Grand Haven, Michigan during Spring.

Figure 1:
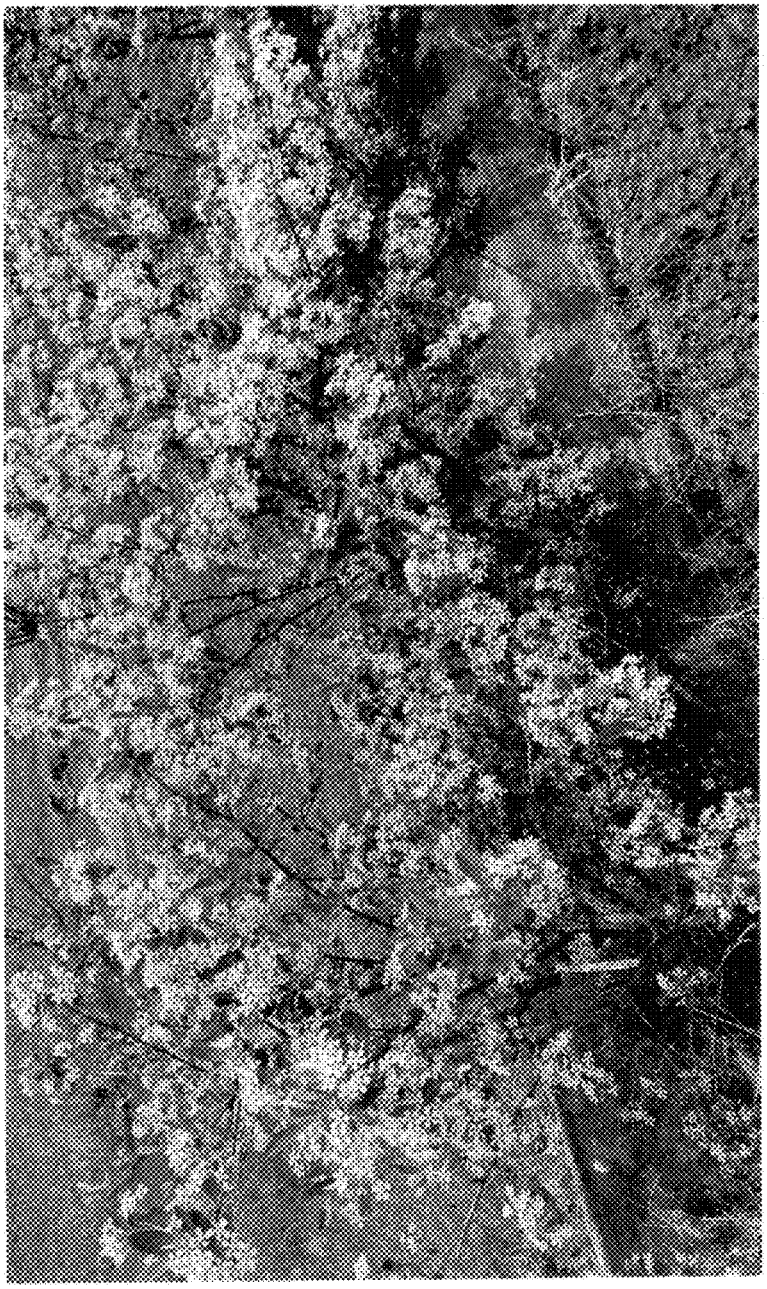
Figure 2:
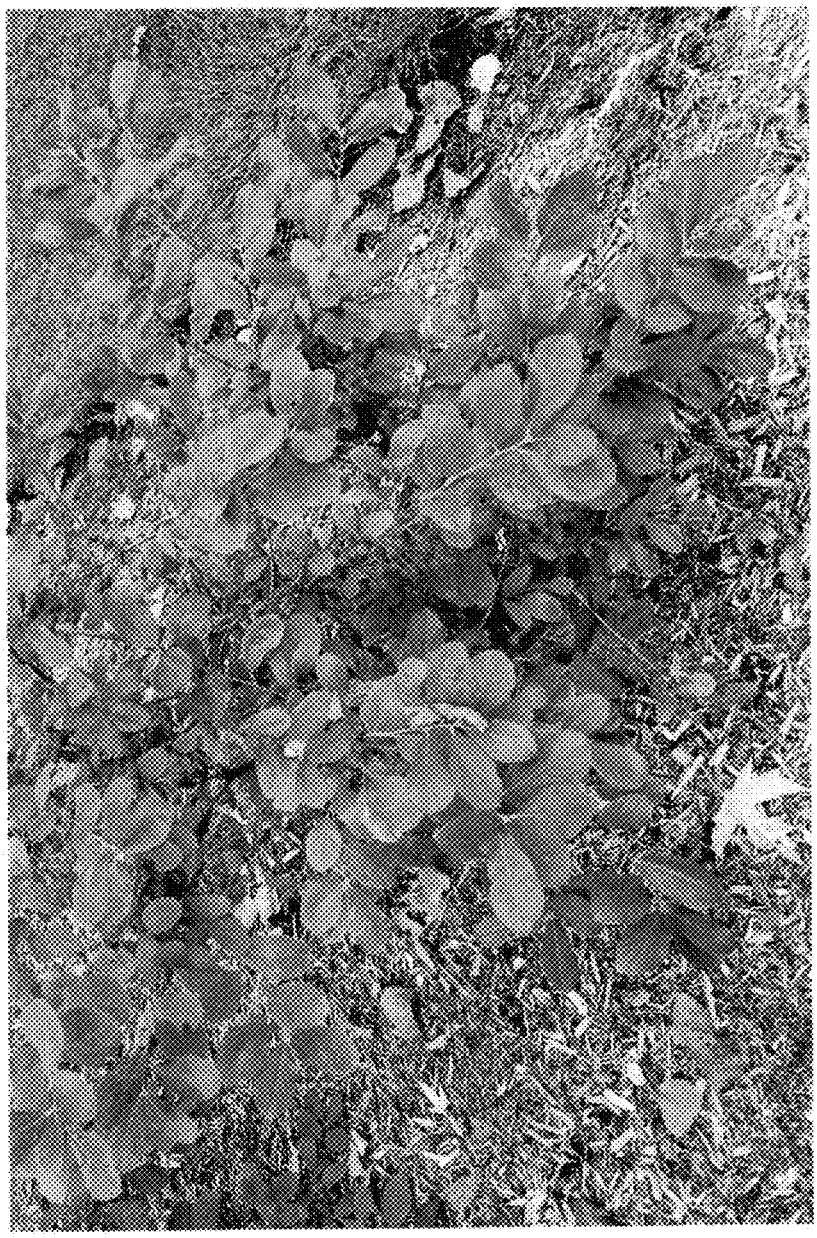
FIG. 2 illustrates in full color a typical field grown plant of 'UCONNAA001' in Grand Haven, Michigan during Summer.
Figure 3:
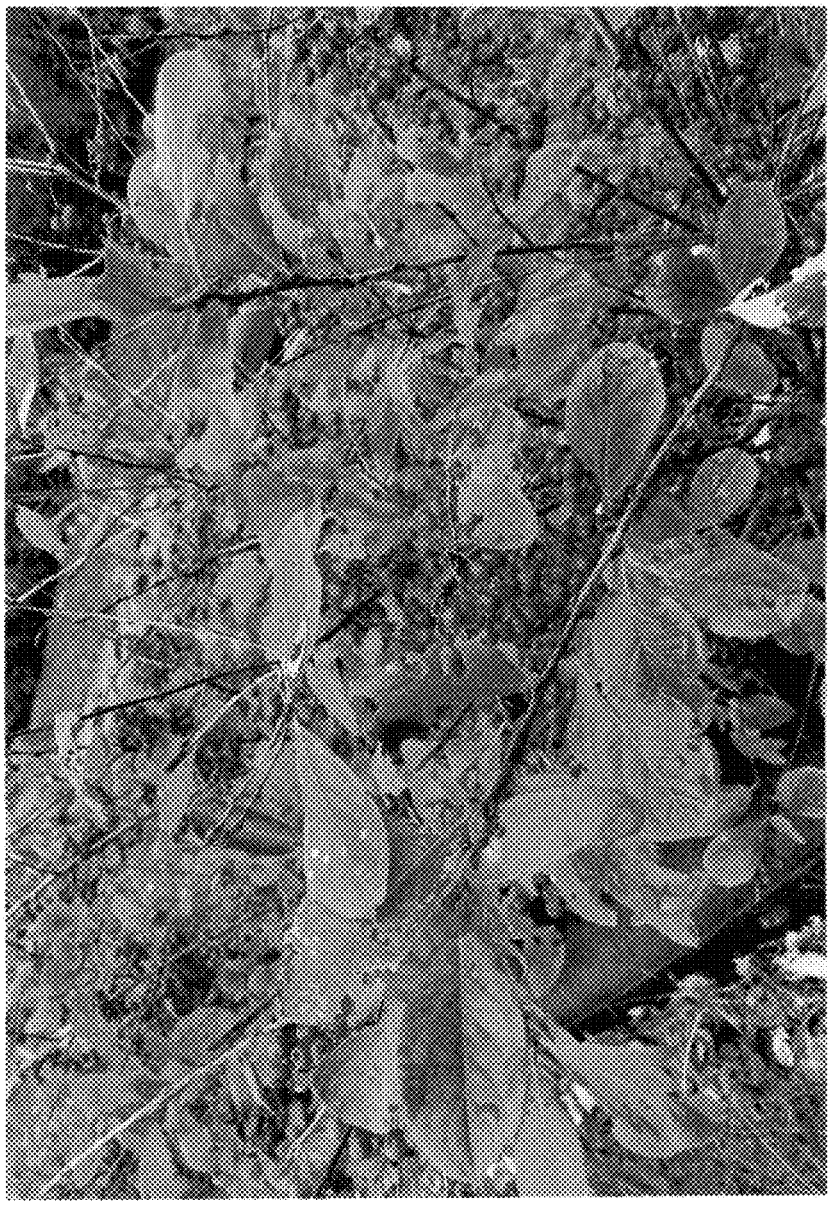
FIG. 3 illustrates a close-up of typical Fall foliage coloration.
Figure 4:
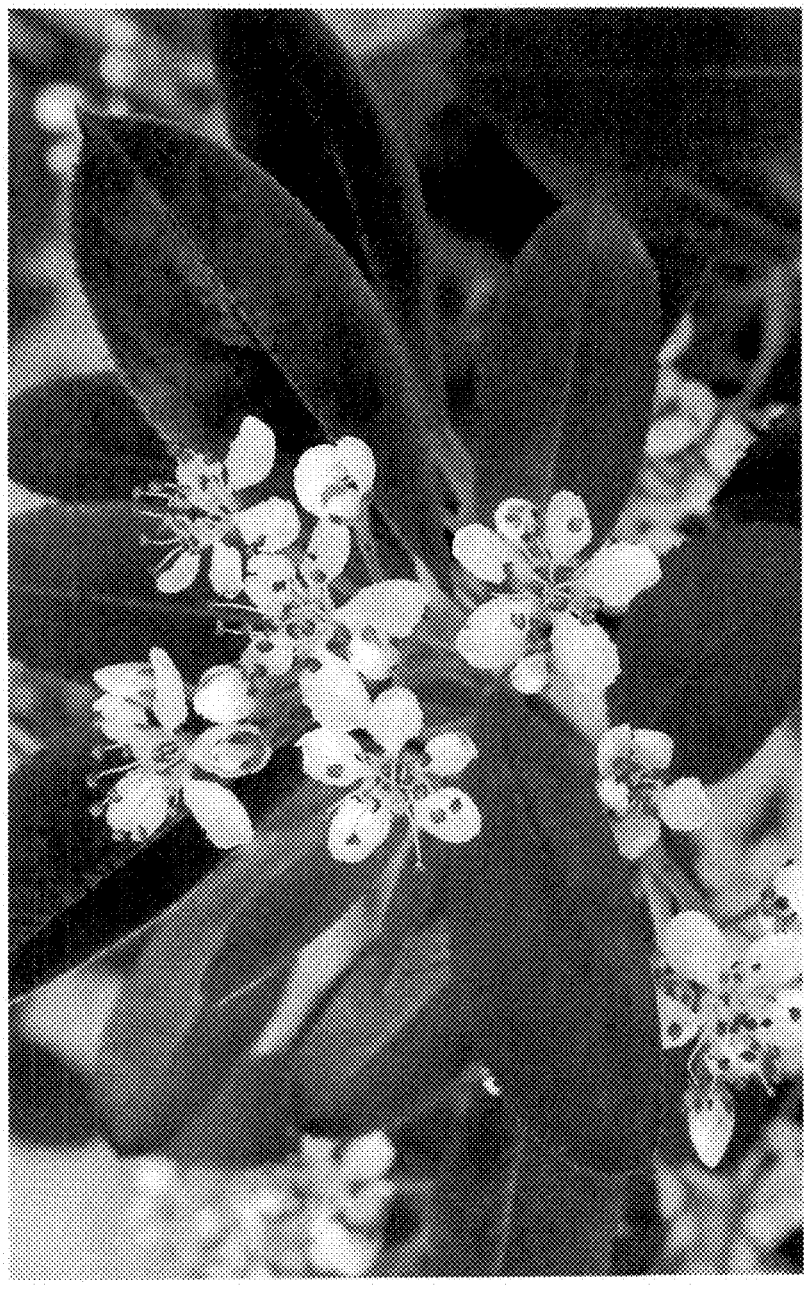
FIG. 4 is a close-up view of typical flowers of 'UCONNAA001'.
Figure 5:
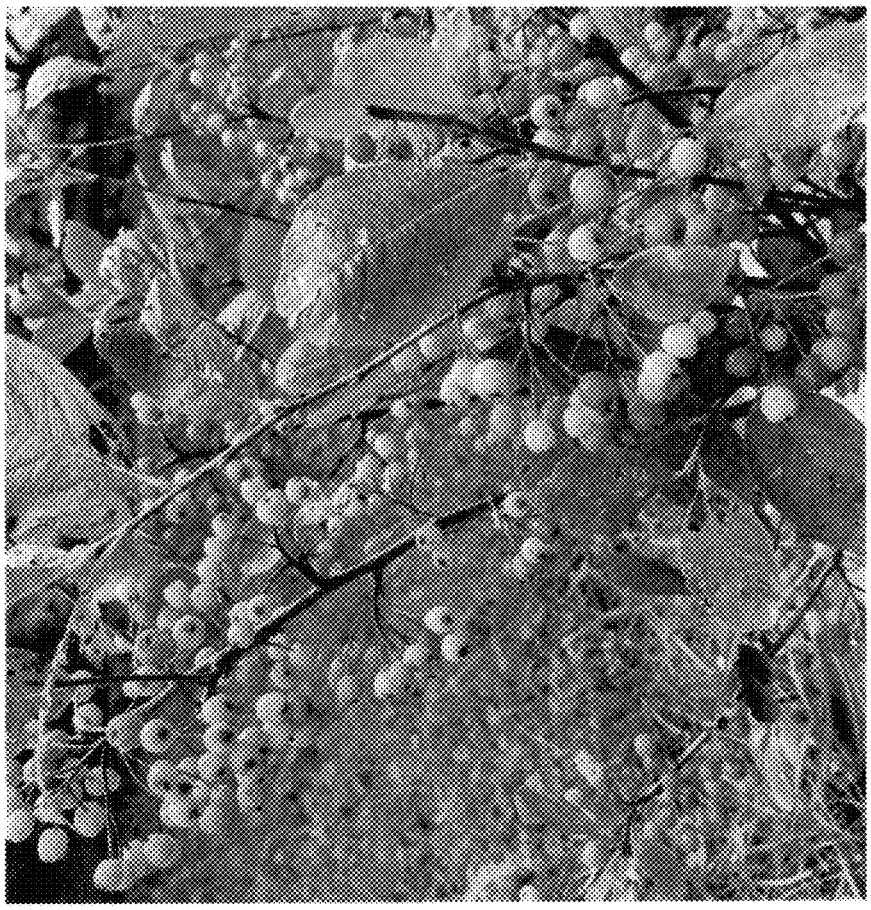
FIG. 5 illustrates ripening fruit.
Figure 6:
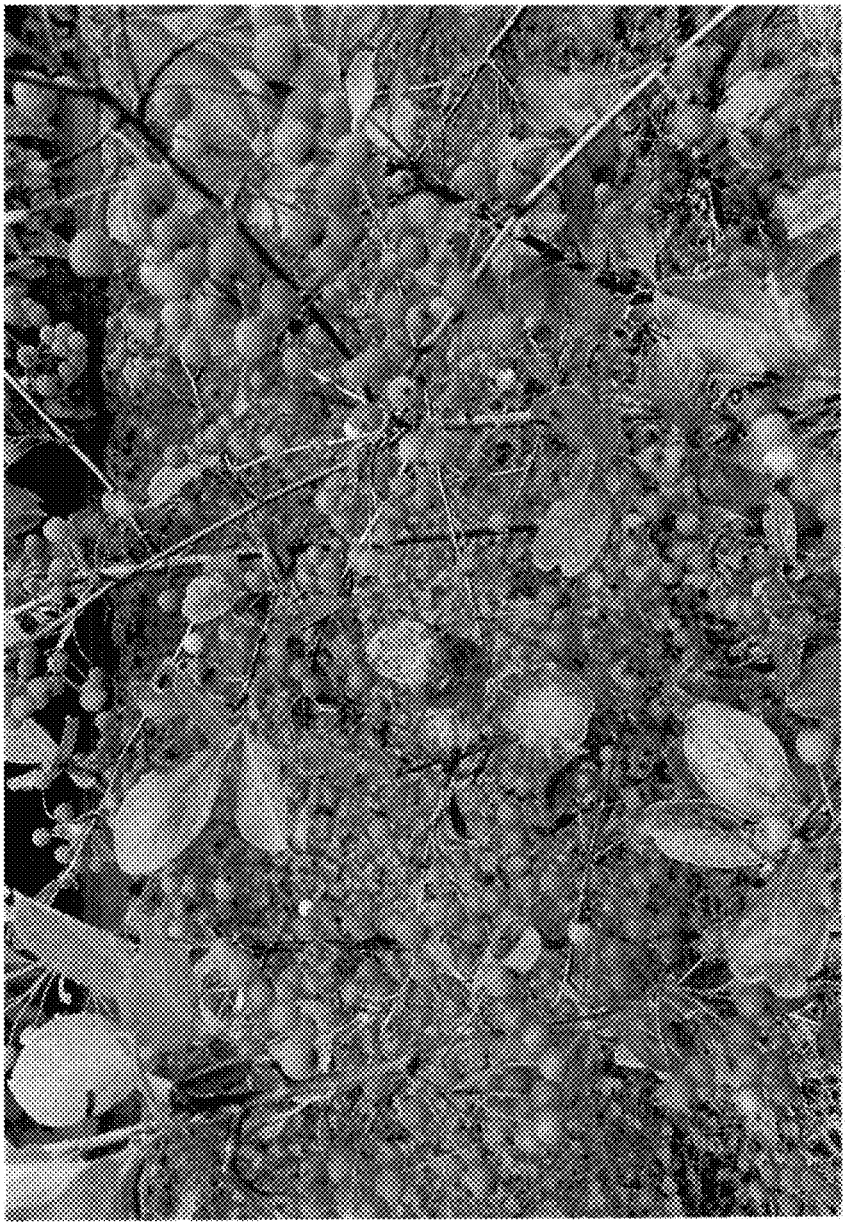
FIG. 6 illustrates mature fruit. All plants depicted are 3 to 4 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'UCONNAA001' plants grown in a poly-house in Grand Haven, Michigan, under natural lighting. Measurements were taken during Summer of 2018. The plants were 3 to 4 years old in 3-gallon containers. The growing temperature ranged from 18° C. to 27° C. during the day, to 5° C. to 10° C. at night. Measurements and numerical values represent averages of typical plant types.

Botanical classification: *Aronia arbutifolia* 'UCONNAA001'.

PROPAGATION

Time to initiate roots: 30 days at 18° C. to 27° C.

Time to produce a rooted young plant: 45 days at 18° C. to 27° C.

Roots: Moderate density, freely branching. Medium thickness, fibrous and fleshy. Brown in color, not accurately measured with The R.H.S. Chart.

PLANT

Plant type: Perennial shrub.

Age of plant described: 3 to 4 years.

Growth habit: Upwards and slightly outwards.

Pot size of plant described: #3.

Appropriate containers sizes: 1, 2, 3 and 5 gallon containers.

Overall plant shape: Upright, loose globular.

Height: 145 cm.

Plant spread: 115 cm.

Growth rate: Moderate to fast.

Plant vigor: Quite to highly vigorous.

Branching characteristics: Basal; minimal pinching to encourage tidy habit.

Length of primary lateral branches: Approximately 121 cm.

Diameter of lateral branches: Approximately 6 mm.

Quantity of lateral branches: About 15 to 20.

Internode length: 2.5 cm.

Stem:

*Stem shape.*—Round.

*Stem strength.*—Strong.

*Aspect.*—45° to 80° from horizontal.

*Stem color.*—New Growth: RHS Yellow-Green 148C. Old Growth: RHS Greyed-Green 197B to Brown 200B.

*Texture.*—Slight pubescence on new growth only.

FOLIAGE

Leaf:

*Arrangement.*—Alternate, single.

*Leaf shape.*—Narrowly elliptic.

*Length.*—6 cm.

*Width.*—2 cm.

*Apex.*—Acuminate.

*Base.*—Attenuate.

*Margin.*—Serrate.

*Texture of top surface.*—Glabrous.

*Texture of bottom surface.*—Pubescent, fuzzy, soft.

*Color.*—Young foliage upper side: RHS Yellow-Green 146A. Young foliage under side: RHS Yellow-Green N148D. Mature foliage upper side: RHS Yellow-Green 147A. Mature foliage under side: Between RHS Yellow-Green 148B and 148C. Fall foliage: RHS Greyed-Red 178A and 180A.

*Venation.*—Pattern: Pinnate. Color upper side: RHS Yellow-Green 146D. Color under side: RHS Yellow-Green 146D.

*Petiole.*—Length: 6 mm. Diameter: 2 mm. Petiole color upper side: RHS Yellow-Green 146D. Petiole color lower side: RHS Yellow-Green 146D. Petiole Texture upper side: Glabrous. Petiole Texture lower side: Slight pubescence.

FLOWER

Natural flowering season: Spring.

Flower arrangement: Compound corymbs along the lengths of lateral branches.

Inflorescence type and habit: Upright, compound corymb.

Inflorescence height: 6 cm.

Inflorescence width: 5 cm.

Quantity of flowers per inflorescence: 18 to 20.

Quantity of flowers per lateral stem: About 400.

Quantity of flower buds per lateral stem: About 100.

Quantity of flowers and buds per plant: About 5,000 to 7,500.

Individual flowers:

*Form.*—Radial/whorl.

*Aspect.*—Upright.

*Diameter.*—1.5 cm.

*Length.*—1.5 cm.

*Depth.*—5 mm.

*Longevity.*—About one week on plant.

*Persistence.*—Self-cleaning.

*Fragrance.*—Sweet, floral, moderate intensity.

Petals:

*Arrangement.*—Stellate.

*Number of petals per flower.*—5.

*Petal fused.*—No.

*Petal shape.*—Broadly elliptic.

*Petal base.*—Attenuate.

*Margin*.—Slightly crenate.
*Tip shape*.—Obtuse.
*Length*.—6 mm.
*Width*.—4 mm.
*Texture*.—Glabrous and silky, upper and lower surfaces.
*Color*.—When opening: Upper surface: RHS White NN155B with a very slight Red-Purple 62D tint. Lower surface: RHS White NN155B with a very slight Red-Purple 62D tint. Fully opened: Upper surface: RHS White NN155B. Lower surface: RHS White NN155B.

Bud:
*Shape*.—Ovoid/elliptic.
*Length*.—6 mm.
*Diameter*.—4 mm.
*Aspect*.—Upright.
*Color*.—RHS White NN155B.

Calyx:
*Shape*.—Collar-like.
*Length*.—6 mm.
*Diameter*.—6 mm.

Sepals:
*Appearance*.—Triangular, inconspicuous.
*Arrangement*.—Stellate.
*Number*.—5.
*Shape*.—Triangular.
*Base*.—Fused.
*Margin*.—Entire.
*Tip shape*.—Acute.
*Length*.—1 mm.
*Width*.—1 mm.
*Color upper*.—RHS Greyed-Orange 177A at tip, fading to Yellow-Green 148C at base.
*Color lower*.—RHS Greyed-Orange 177A at tip, fading to Yellow-Green 148C at base.
*Texture, upper side*.—Glabrous.
*Texture, lower side*.—Slightly pubescent.

Peduncle:
*Length*.—4.5 cm.
*Diameter*.—2 mm.
*Angle*.—45° relative to lateral stem.
*Color*.—RHS Yellow-Green 148C.
*Strength*.—Strong.
*Texture*.—Slightly pubescent.

Pedicels:
*Length*.—8 mm.
*Diameter*.—1 mm.
*Angle*.—45° to 60° relative to peduncle.
*Color*.—RHS Yellow-Green 148C.
*Strength*.—Strong and somewhat flexible.
*Texture*.—Slightly pubescent.

REPRODUCTIVE ORGANS

Stamens:
*Number*.—18 to 20.
*Filament length*.—3 mm.
*Filament color*.—RHS White NN155B.

Anthers:
*Shape*.—Elliptic.
*Length*.—1 mm.
*Color*.—RHS Greyed-Red 184C.
*Pollen color*.—RHS Yellow-White 158B.
*Pollen amount*.—Moderate.

Pistil:
*Number*.—5.
*Length*.—5 mm.
*Style*.—Length: 5 mm. Color: RHS Yellow-Green 145C.
*Stigma*.—Shape: Rounded. Color: RHS Yellow-Green 145C. Ovary Color: RHS Yellow-Green 145C.

FRUIT AND SEED

Fruit:
*Quantity per lateral branch*.—100 to 200.
*Quantity per plant*.—1500 to 4000.
*Length*.—7 mm.
*Diameter*.—7 mm.
*Shape*.—Globose.
*Color*.—Emerging RHS Yellow-Green N144A, maturing to Red 46A.
*Texture*.—Smooth-skinned, fleshy.

Seeds:
*Quantity per flower*.—6.
*Shape*.—Elliptic.
*Length*.—3 mm.
*Diameter*.—1.5 mm.
*Color*.—RHS Greyed-Orange 163B.

OTHER CHARACTERISTICS

Disease/pest resistance: Neither resistance nor susceptibility to normal diseases and pests of *Aronia* observed.

Temperature tolerance: Tolerant to USDA Zones 4-9.

What is claimed is:

1. A new and distinct cultivar of *Aronia arbutifolia* plant named 'UCONNAA001' as illustrated and described herein.

* * * * *